United States Patent
Kitagawa et al.

(10) Patent No.: US 9,193,635 B2
(45) Date of Patent: Nov. 24, 2015

(54) REDUCING MIXTURE DERIVED FROM MICROORGANISMS WHICH HAS AN OXIDATION-REDUCTION POTENTIAL OF 0 MV OR LESS, AND PRODUCTION METHOD FOR SAME

(75) Inventors: Takanori Kitagawa, Moriya (JP); Chikako Iwabuchi, Moriya (JP); Daiki Honma, Moriya (JP); Yoshio Maekawa, Miki (JP)

(73) Assignee: Asahi Group Holdings, Ltd., Tokyo (JP)

( * ) Notice: Subject to any disclaimer, the term of this patent is extended or adjusted under 35 U.S.C. 154(b) by 807 days.

(21) Appl. No.: 13/254,557

(22) PCT Filed: Mar. 15, 2010

(86) PCT No.: PCT/JP2010/054342
§ 371 (c)(1),
(2), (4) Date: Sep. 2, 2011

(87) PCT Pub. No.: WO2010/104197
PCT Pub. Date: Sep. 16, 2010

(65) Prior Publication Data
US 2011/0319264 A1    Dec. 29, 2011

(30) Foreign Application Priority Data
Mar. 13, 2009  (JP) ................. 2009-061841

(51) Int. Cl.
| C05F 5/00 | (2006.01) |
| A01N 63/04 | (2006.01) |
| C05C 9/00 | (2006.01) |

(Continued)

(52) U.S. Cl.
CPC ............. *C05F 5/008* (2013.01); *A01N 63/04* (2013.01); *C05C 9/00* (2013.01); *C09K 17/16* (2013.01); *C09K 17/32* (2013.01); *C12N 1/18* (2013.01)

(58) Field of Classification Search
CPC .................. A01N 63/04; C05F 5/008
See application file for complete search history.

(56) References Cited

U.S. PATENT DOCUMENTS

| 5,834,275 A | 11/1998 | Raehse et al. |
| 2002/0078623 A1 | 6/2002 | Raddon |

(Continued)

FOREIGN PATENT DOCUMENTS

| CN | 101314163 A | 12/2008 |
| EP | 1170354 A1 | 1/2002 |

(Continued)

OTHER PUBLICATIONS

Jukes (Journal of the Institute of Brewing 1941, 47(2), 61-63).*

(Continued)

*Primary Examiner* — Abigail Fisher
*Assistant Examiner* — Jessica Kassa
(74) *Attorney, Agent, or Firm* — Marshall, Gerstein & Borun LLP

(57) ABSTRACT

Disclosed is a processing method whereby microorganisms, particularly waste yeast, can be turned into a processed material having high added value. Also disclosed is said processed material. Further disclosed is a production method for a reducing mixture derived from microorganisms which has an oxidation-reduction potential of 0 mV or less, said method being characterized by processing microorganisms or components thereof with superheated steam in the absence of oxygen.

4 Claims, 14 Drawing Sheets

(51) Int. Cl.
*C09K 17/16* (2006.01)
*C09K 17/32* (2006.01)
*C12N 1/18* (2006.01)

(56) References Cited

U.S. PATENT DOCUMENTS

2005/0112255 A1 5/2005 Tottenham et al.
2006/0204638 A1 9/2006 Chen et al.

FOREIGN PATENT DOCUMENTS

| GB | 1129785 | * 10/1968 | ............... A23K 1/00 |
|---|---|---|---|
| JP | 52076413 A | 6/1977 | |
| JP | 62224281 A | 10/1987 | |
| JP | 6040832 A | 2/1994 | |
| JP | 11056288 A | 3/1999 | |
| JP | 2004284858 A | 10/2004 | |
| JP | 2005185187 A | 7/2005 | |
| TW | 200631508 | 3/2007 | |

OTHER PUBLICATIONS

Deventer et al. (Drying Technology, 2001, 19(8), 2033-2045).*
Elustondo et al. (Drying Technology 2002, 20(2), 381-402).*
Hu et al., "A Preliminary Study on the Resistance Mechanism of Poplar Cell Induced by *Dothiorella gregaria* Cell Wall Oligosaccharide Elicitor," Journal of Northwest Sci-Tech University of Agriculture and Forestry, 31(4):145-148 (2003). Abstract Only.
International Search Report for PCT/JP2010/054342 dated Apr. 13, 2010.
Written Opinion for PCT/JP2010/054342 dated Apr. 13, 2010.
Suzuki, "Food Processing Using Superheated Steam Food Processing Using Superheated Steam and Its Treatment Characteristics," The Food Industry, 48:29-33 (Jun. 30, 2005).
Abe, "Applications to the Food Processing with Superheated Steam," Food Processing and Ingredients, 43:8-10 (Dec. 1, 2008).
Iwabuchi et al., "Effect of yeast extract (A15) on fruit quality of strawberry," Horticultural Research (Japan), 7:365 (2008).
Shiral et al., "Effect of yeast extract (A15) on growth of high brix tomato," 75:357 (Mar. 29, 2006).
Kitagawa et al., "Induction of resistance to crown and root rot and powdery mildew on tomato by yeast extract," 74:413 (Oct. 1, 2005).
Takasaki et al., "Effect of yeast extract under the high temperature stress on growth and yield of tomato and cabbage," Horticultural Research (Japan), 74:161 (Oct. 1, 2005).
Takasaki et al., "Effect of yeast extract (A15) on growt of radish and lettuce," 75:335 (Mar. 29, 2006).
Head et al., "Effects of Superheated Steam on Geobacillus Stearothermophilus Spore Viability", Journal of Applied Microbiology 104, 2008, pp. 1213-1220.
Cenkowski et al., "Decontamination of Food Products with Superheated Steam", Journal of Food Engineering 83, 2007, pp. 68-75.
Search Report in EP Application No. 10750943.2 dated Sep. 11, 2014.
Chien et al., "Effect of Aeration on the Ethanol Production by *Saccharomyces cerevisiae* in Very-High-Gravity (VHG) Fermentation," Thesis for Master of Science Department of Bioengineering Tatung University (2009).
Jiang, "Current Situation of the Use of Plant Nutrition Agent and the Issue of Phytotoxicity," Special Report by Taiwan Agricultural Chemicals and Toxic Substances Research Institute, pp. 8-19 (2005).
Oeztuerk et al., "Influence of Living and Autoclaved Yeasts of *Saccharomyces boulardil* on In Vitro Ruminal Microbial Metabolism," *J. Dairy Sci.*, 88:2594-2600 (2005).
Australian Patent Examination Report for Application No. 2010221982 dated Dec. 10 2012.

* cited by examiner

OXIDATION-REDUCTION POTENTIAL OF ANAEROBIC MICROORGANISM-DERIVED REDUCING MIXTURE AND OF KOJI MOLDS AND SHOCHU YEAST-DERIVED REDUCING MIXTURE

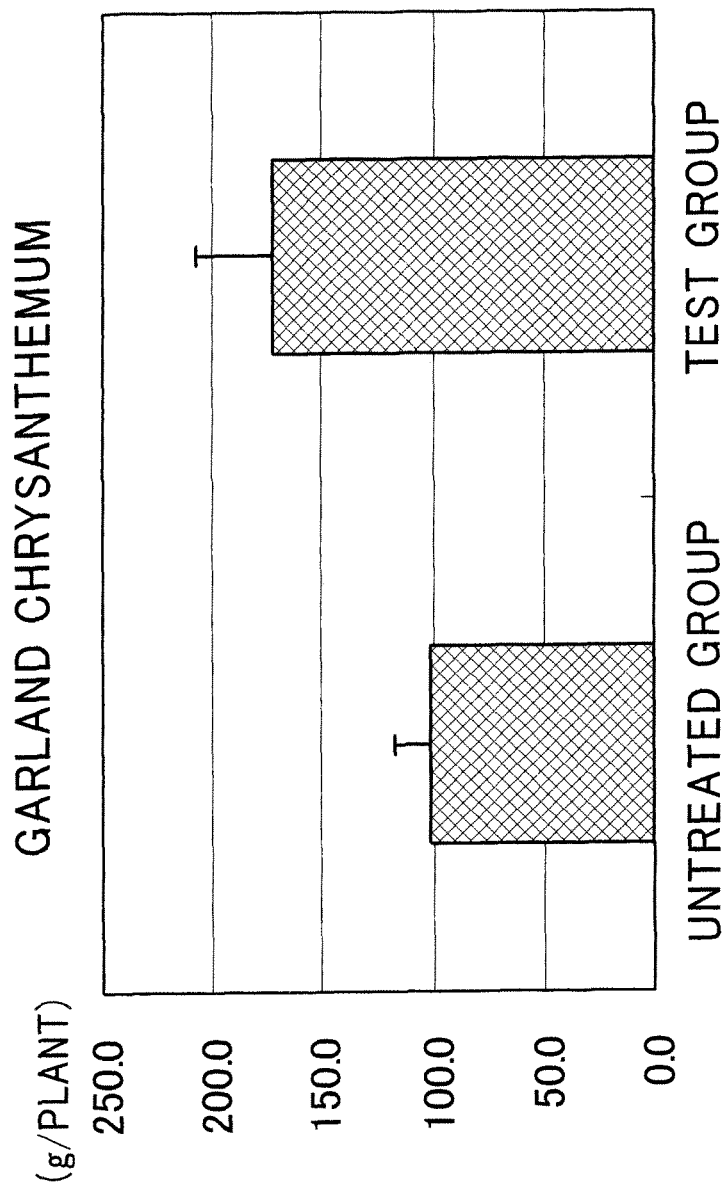

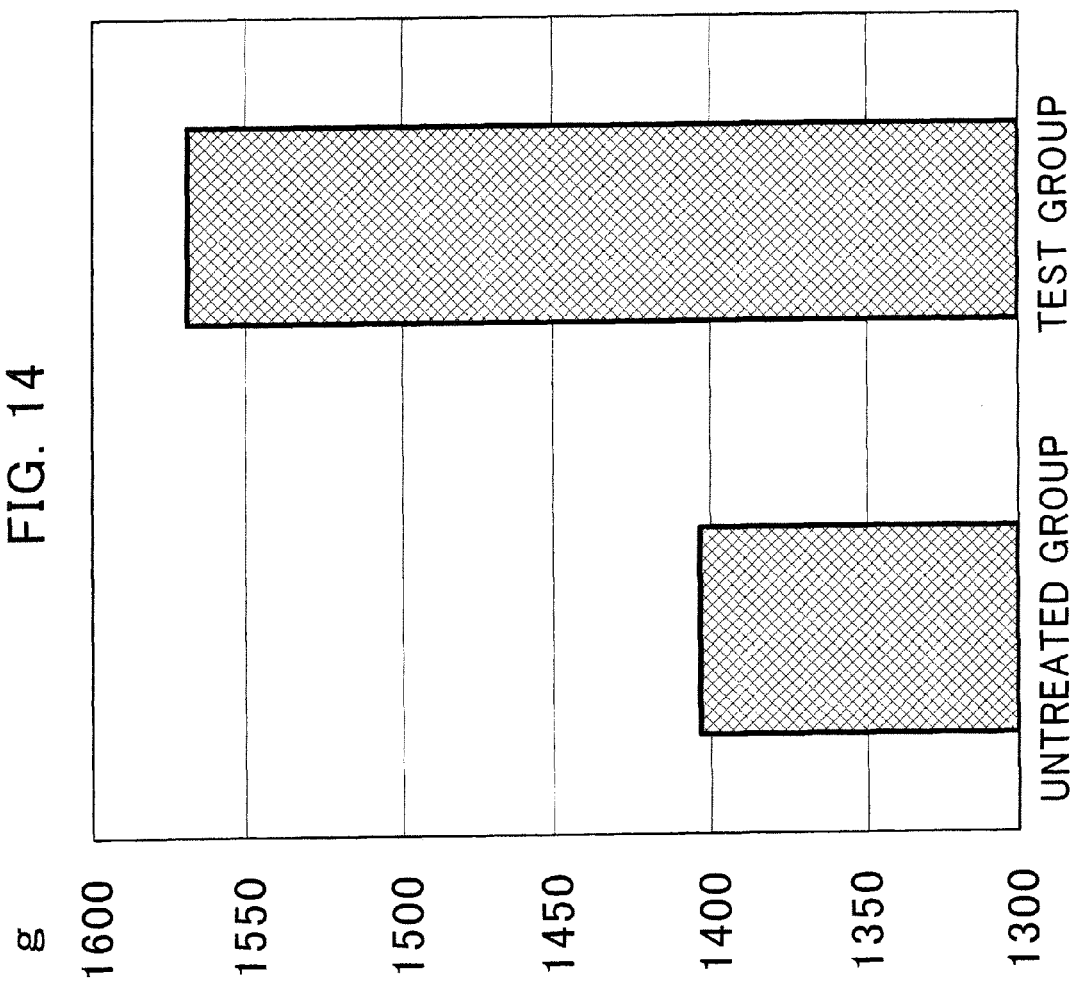

REDUCING MIXTURE DERIVED FROM MICROORGANISMS WHICH HAS AN OXIDATION-REDUCTION POTENTIAL OF 0 MV OR LESS, AND PRODUCTION METHOD FOR SAME

TECHNICAL FIELD

The present invention relates to a microorganism-derived reducing mixture obtained by subjecting a microorganism to a hydrothermal treatment and a method for producing the mixture.

BACKGROUND ART

Waste yeast discharged from food production plants such as breweries is subjected to waste treatments by incineration or the like, except for part of the waste yeast being used as a raw material for yeast extracts and yeast preparations, feeds for livestock, fertilizers, and the like. Meanwhile, a portion of yeast cell walls remaining after extraction of yeast extracts is mainly discarded while the other portion of the yeast cell walls is used for health foods, feeds for livestock, and the like.

However, the waste treatments entail costs of transport to disposal sites and disposal costs. Moreover, in the cases where the waste yeast is used for the above-described foods, feeds, fertilizer, and the like, conventional usages have some limitations in terms of the applications, the amount used, and the added values of products, when the amount of the waste yeast generated is taken into consideration. Hence, there are expectations for a treated material which can be used for new applications, can increase the amount used, and has higher added values, and for a treatment method therefor.

Patent Literature 1 describes a method for obtaining an intracellular substance by destroying cells with high-temperature high-pressure steam, and shows yeast as a preferred microorganism. Since the reaction is conducted in a low-temperature region, which is an ionization reaction region, decomposition to low-molecular weight substances hardly proceeds, and the amount of reducing substances produced is very small. Hence, it is difficult to keep the intrinsic potential within a reducing region.

Patent Literature 2 describes a method for obtaining a water-soluble fraction of cell walls of a microorganism by use of high-temperature and high-pressure water at a temperature higher than 100° C. and at a pressure not higher than the saturation vapor pressure at the temperature, and shows yeast as the microorganism. The water-soluble fraction obtained by the method has an oxidation-reduction potential of 0 mV or less immediately after being obtained, but soon the oxidation-reduction potential turns to 0 mV or higher.

CITATION LIST

Patent Literatures

Patent Literature 1: Japanese Patent Application Publication No. Sho 62-224281
Patent Literature 2: Japanese Patent Application Publication No. 2005-185187

SUMMARY OF INVENTION

The present invention has been made in view of the above-described circumstances, and an object of the present invention is to provide a treatment method which enables conversion of a microorganism, particularly waste yeast into a treated material having a high added value, and to provide the treated material.

The present invention provides a method for producing a microorganism-derived reducing mixture having an oxidation-reduction potential of 0 mV or less, the method comprising subjecting a microorganism or a microorganism component to a superheated steam treatment in the absence of oxygen.

In addition, the present invention provides a method for producing a microorganism-derived reducing mixture having an oxidation-reduction potential of 0 mV or less, the method comprising subjecting a microorganism or a microorganism component to a superheated steam treatment in the presence of silicic acid or a silicate.

In addition, the present invention provides a microorganism-derived reducing mixture having an oxidation-reduction potential of 0 mV or less, the microorganism-derived reducing mixture being obtained by any one of the production methods.

In addition, the present invention provides a microorganism-derived reducing mixture having an oxidation-reduction potential of 0 mV or less, wherein a rise in oxidation-reduction potential 14 days after preparation of said mixture is 40% or less of a lowest potential.

In addition, the present invention provides a composition comprising the microorganism-derived reducing mixture.

In addition, the present invention provides a soil quality improver composition comprising the microorganism-derived reducing mixture.

In addition, the present invention provides a plant disease resistance improver composition comprising the microorganism-derived reducing mixture.

Moreover, the present invention provides a plant growth promoter comprising the microorganism-derived reducing mixture.

The reducing substance obtained by the present invention has a reducing ability. Hence, when the reducing substance is used for agricultural plants, the reducing substance can be introduced in a state close to the oxidation-reduction potential in the cells, so that enhancement of the functionality of the substance can be expected. The reducing substance can also be used for the flooding technology, which is one of the soil sterilization technologies. Moreover, since the reducing substance has anti-oxidation activities such as SOD inhibition, it can be expected that the reducing substance will be applied to anti-aging agents for the skin, and the like by utilizing the anti-oxidation ability.

BRIEF DESCRIPTION OF DRAWINGS

FIG. 13 is a graph showing comparison of the weights of the edible part of garland *chrysanthemum* in Example 14.

FIG. 14 is a graph showing comparison of the yields of cherry tomato in Example 17.

DESCRIPTION OF EMBODIMENTS

Figure 1:
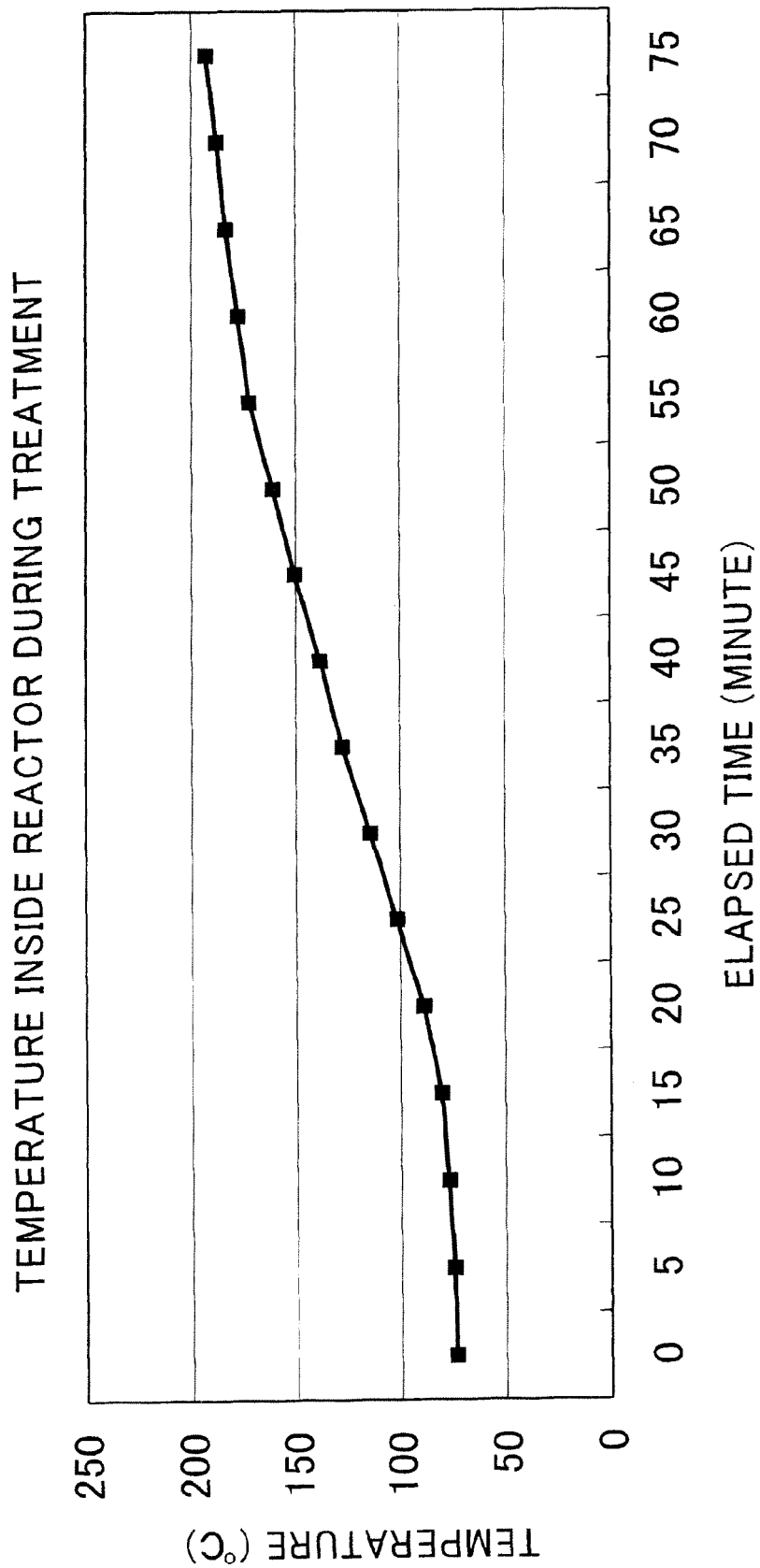
FIG. 1 is a graph showing change with time of the temperature inside a reactor due to superheated steam in Example 1.

A method for producing a microorganism-derived reducing mixture of the present invention comprises subjecting a microorganism or a microorganism component to a superheated steam treatment.

The microorganism used in the present invention is not particularly limited, and yeasts which have been eaten and the like are preferable from the viewpoint of safety. When the yeasts and the like are used for fertilizers, animal feeds, foods, beverages, supplements, drugs, and the like, it can be expected that consumers will readily accept these products because of the high safety. As the yeasts, yeasts cultured for this purpose only may be used. However, the use of a yeast obtained as a surplus waste material from the brewing industries of beer, sake, soybean paste, soy sauce, or the like is advantageous in terms of reduction in amount of waste materials and in waste disposal costs. For example, a brewer's yeast, which can be supplied stably and industrially, is particularly preferable.

The form of the microorganism used may be a yeast as a whole. Alternatively, a yeast extract or a microorganism component such as, for example, yeast cell walls remaining after production of a yeast extract can be used. The state of the yeast, the yeast extract, the yeast cell walls, or the like may be any, and, for example, the state may be a slurry, one whose water content is reduced by pressing, one whose water content is further reduced by drying, a powder, a suspension, or the like. A brewer's yeast slurry, a pressed brewer's yeast, a dry brewer's yeast, a brewer's yeast suspension, dry yeast cell walls, a yeast cell wall suspension, and a brewer's yeast-containing inorganic material are preferable.

In the present invention, the superheated steam refers to steam at a temperature higher than 100° C. In the present invention, the superheated steam treatment is conducted with superheated steam at preferably 120° C. to 220° C., more preferably 150° C. to 210° C. Moreover, the superheated steam treatment is conducted with superheated steam at preferably 0.9 MPa to 1.9 MPa, more preferably 1.2 MPa to 1.8 MPa. The superheated steam treatment is conducted preferably with superheated steam at a pressure of 0.9 MPa to 1.9 MPa and at 120° C. to 220° C., and more preferably with superheated steam at a pressure of 1.2 MPa to 1.8 MPa at 150° C. to 210° C. In the present invention, the superheated steam treatment is conducted in the absence of oxygen. Examples of a method for conducting the superheated steam treatment in the absence of oxygen include a method in which the gas inside a reaction vessel is replaced with a gas such as carbon dioxide gas, nitrogen gas, or argon, and the like. In the present invention, the superheated steam treatment may be conducted in the presence of silicic acid or a silicate. As the silicic acid or the silicate used, a diatom-derived siliceous ore, which is inexpensive and has a stable pore volume, can be used. The silicic acid or the silicate used in the superheated steam treatment is not particularly limited, and examples thereof include silicic acid, silicates, and the like such as zeolite and acid clay, which are classified into that.

The amount of the silicic acid or the silicate added is preferably 1 w/w % to 40 w/w %, and more preferably 15 w/w % to 20 w/w %. Note that, the added amount is to be adjusted as appropriate depending on the quality of the yeast and the concentration of the yeast at the time of being used for the treatment.

The microorganism-derived reducing mixture obtained by the above-described method of the present invention has an oxidation-reduction potential of 0 mV or less. The microorganism-derived reducing mixture of the present invention has preferably an oxidation-reduction potential of −50 mV or less. Moreover, the microorganism-derived reducing mixture obtained by the above-described method of the present invention is such that a rise in oxidation-reduction potential 14 days after preparation of said mixture is 40% or less of a lowest potential. The microorganism-derived reducing mixture of the present invention is preferably such that the percentage of the rise in oxidation-reduction potential 14 days after preparation of said mixture is 35% or less, and more preferably such that the percentage of the rise in oxidation-reduction potential 14 days after preparation of said mixture is 10% or less.

Moreover, the oxidation-reduction potential of the microorganism-derived reducing mixture according to the present invention may be 0 mV or positive in the period from immediately after to 1 or 2 days after the treatment. However, the oxidation-reduction potential gradually lowers, turns to a negative value in 3 to 4 days, and remains stably at a negative value.

The oxidation-reduction potential in respiration cells of eukaryotes is around −180 mV. Hence, the microorganism-derived reducing mixture of the present invention, which is converted into a reducing substance, has an excellent affinity for the insides of cells, and enables the yeast-derived component to act effectively.

Moreover, since a brewer's yeast or the like is used as the raw material, the quality stability of the raw material can be secured, and conversion into a high-value added product can be expected. By adding a novel production technology to basic technologies accumulated so far, such a raw material can be applied to various fields as a reducing material.

In the case of use in the agricultural field, a yeast-derived component known so far is produced in the reducing form, and introduced in a state close to an oxidation-reduction potential in cells of agricultural plants. Thus, the functionality of the substance can be enhanced. As a result, it is possible to obtain effects such as growth promotion, yield increase, and enhancement of plant disease resistance.

Moreover, by exploiting the fact that the microorganism-derived reducing mixture is a reducing substance, the microorganism-derived reducing mixture can be used for a flooding reduction technology, which is a noticeable soil sterilization technology. The flooding reduction technology is a method in which water is kept on soil as in the case of a paddy field, and the state of the soil under the water surface is changed to a reduced state to thereby reduce pathogens in the soil. However, the flooding reduction technology lacks versatility, for example, because a large amount of water is necessary, water needs to be kept for a long period, and the technology can be implemented only in the high temperature period because of the mediation of microorganisms. Moreover, the flooding rather leads to proliferation of pathogens in some cases. When the substance of the present invention is used as a soil improver composition, the reducing ability of the substance itself can be used. Hence, it is possible to control the potential in soil to −200 mV or less, irrespective of the temperature. Accordingly, the microorganism-derived reducing mixture of the present invention can be used to prepare a soil quality improver composition. In addition to the microorganism-derived reducing mixture of the present invention, the soil quality improver composition may contain any of humic substances, zeolite, diatomite, calcium silicate, vermiculite, and peat mosses, which are used for soil improvement. Soil improvement by use of the soil quality improver composition is expected to achieve effects such as growth promotion and yield increase.

In contrast to conventionally provided reducing materials, the treated product has such an excellent anti-oxidation ability and stability that the oxidation-reduction potential of the treated product is stably retained at a negative potential for a long period. Accordingly, the microorganism-derived reducing mixture of the present invention can be used to prepare a cosmetic composition. In addition to the microorganism-derived reducing mixture of the present invention, any other generally usable cosmetic components can be used for the cosmetic composition, and the cosmetic components can be selected from the following substances depending on the efficacy, and the effect. Examples thereof include excipients, fragrances, and the like which are generally used for cosmetics, as well as various cosmetic components such as fats and fatty oils, surfactants, humectants, whitening agents, pH adjusters, binders, polyvalent alcohols, essential oils, fragrances, thickeners, preservatives, antioxidants, ultraviolet absorbers, pigments, pulverized plant materials, crude drugs, inorganic salts, inorganic acids, detergents, emulsifiers, and the like.

Moreover, the microorganism-derived reducing mixture of the present invention can be used for feeds for livestock, fishes, and the like, for improvement of skin symptoms caused by active oxygen (moistness, dryness, dullness in color, blemishes, freckles, sagging, wrinkles, texture of the skin, firmness, and the like), for prevention or treatment of diseases such as cerebral stroke, arteriosclerosis, myocardial infarction, rheumatism, inflammation, stomach ulcer, cataract, cancer, AIDS, and the like, for prevention of aging, and for a hair restorer, for example.

Moreover, since the aforementioned method of the present invention can suppress the Maillard reaction during the treatment, the treated product is less colored, and expected to be used for a wider range of applications.

The microorganism-derived reducing mixture of the present invention can be used to prepare a plant disease resistance improver composition. In addition to the microorganism-derived reducing mixture of the present invention, the plant disease resistance improver composition can be blended with components such as water-soluble solvents and surfactants, as long as the effect of improving the resistance to diseases, pests, and nematodes achieved by the microorganism-derived reducing mixture of the present invention is not impaired.

Moreover, a material containing one or more substances having elicitor activities selected from peptides, polysaccharides, glycoproteins and lipids can also be added to the plant disease resistance improver composition. Various substances specific to individual plants have been known as the substances having elicitor activities, and the substances having elicitor activities may be selected as appropriate depending on the plant to be subjected.

Moreover, a plant growth control agent can also added to the plant disease resistance improver composition.

In general, organisms are affected by the oxidation-reduction potential of their growing environments. It can be said that those which prefer environments with high oxidation-reduction potentials are aerobic, whereas those which prefer environments with low oxidation-reduction potentials are highly anaerobic. Methanogens are well known as organisms which require particularly high anaerobic states, and the oxidation-reduction potential of culture media for methanogens needs to be −330 mV or less. In addition, ordinary nitrifying bacteria, denitrifying bacteria, sulfate-reducing bacteria, and the like require low oxidation-reduction potentials. Examples of organisms which prefer aerobic environments include almost all animals, almost all fungi, some bacteria such as bacteria of the genus *Bacillus*, the genus *Pseudomonas*, and the like, nematodes, and the like. As described above, individual microorganisms have their respective preferred regions of oxidation-reduction potential. By controlling the oxidation-reduction potential, specific microorganisms can be activated or inactivated. When an environment with a low oxidation-reduction potential is created by use of the microorganism-derived reducing mixture of the present invention, the activities of microorganisms which prefer aerobic environments can be suppressed. Hence, the microorganism-derived reducing mixture can be used as a fungicide, an antiviral agent, or the like. In the same manner, microorganisms which prefer anaerobic environments can be activated. Hence, the microorganism-derived reducing mixture of the present invention can be used for culturing of lactic acid bacteria, methanogens, and the like; brewing of alcoholic beverages by anaerobic fermentation such as brewing of beer; production of lactic acid bacteria beverages; and the like.

When used for skin symptom improvement, the microorganism-derived reducing mixture of the present invention can be prepared, for example, in the form of a supplement. A known method may be employed for the preparation. The dosage form is not particularly limited, and examples thereof include oral preparations including solid preparations such as a tablet, a powder, fine granules, granules, a capsule, and a pill; and liquid preparations such as an aqueous solution, a suspension, a syrup, and an emulsion; and the like. These oral preparations can be produced by a generally employed method. Here, any of excipients, disintegrators, binders, lubricants, surfactants, alcohols, water, water-soluble polymers, sweeteners, corrigents, acidulants, drug carriers, and the like which are generally used in the art may be added to the oral preparations depending on the forms thereof.

Moreover, a beverage for skin symptom improvement can be produced by blending the microorganism-derived reducing mixture of the present invention with a beverage. Examples of the beverage include fruit juices, vegetable juices, roasted barley tea, green tea, black tea, coffee, yogurt beverages, lactic acid bacteria beverages, low-alcoholic beverages, and the like. By drinking the beverage with which the microorganism-derived reducing mixture of the present invention is blended, the above-described skin symptoms are prevented or improved safely.

Moreover, a food for skin symptom improvement can be produced by blending the microorganism-derived reducing mixture of the present invention with a food. Examples of the food include dairy products such as fermented milk, cheese, and butter; confectionery products such as candies, cookies, chewing gum, butter cake; breads; and the like. By taking the food with which the microorganism-derived reducing mixture of the present invention is blended, the above-described skin symptoms are prevented or improved safely.

Moreover, a skin cosmetic can be produced. Examples of the skin cosmetic include lotion, emulsion, cosmetic cream, foundation, rouge, face powder, and the like. The skin cosmetic may be prepared according to an ordinary method. By use of a skin cosmetic with which the microorganism-derived reducing mixture of the present invention is blended, the above-described skin symptoms are prevented or improved.

Moreover, a skin cosmetic can be produced by blending the microorganism-derived reducing mixture of the present invention. Examples of the skin cosmetic include lotion, emulsion, cosmetic cream, foundation, rouge, face powder, and the like. The skin cosmetic may be prepared according to an ordinary method. By using the skin cosmetic with which the microorganism-derived reducing mixture of the present invention is blended, the above-described skin symptoms are prevented or improved.

Furthermore, a pharmaceutical preparation for skin symptom improvement containing the microorganism-derived reducing mixture of the present invention as an active ingredient can be produced. The dosage form of the pharmaceutical preparation for skin symptom improvement of the present invention is not particularly limited, and example thereof include oral preparations including solid preparations such as a tablet, a powder, fine granules, granules, a capsule, a pill, and the like; liquid preparations such as an aqueous solution, a suspension, a syrup, and an emulsion; and the like. These oral preparations can be produced by a generally employed method. Here, any of excipients, disintegrators, binders, lubricants, surfactants, alcohols, water, water-soluble polymers, sweeteners, corrigents, acidulants, drug carriers, and the like which are generally used in the art may be added to the oral preparations depending on the forms thereof. By taking the pharmaceutical preparation for skin symptom improvement containing the microorganism-derived reducing mixture of the present invention as an active ingredient, the above-described skin symptoms are prevented or improved.

EXAMPLES

Example 1

Production of Brewer's Yeast-Derived Reducing Mixture in the Absence of Oxygen

Figure 2:
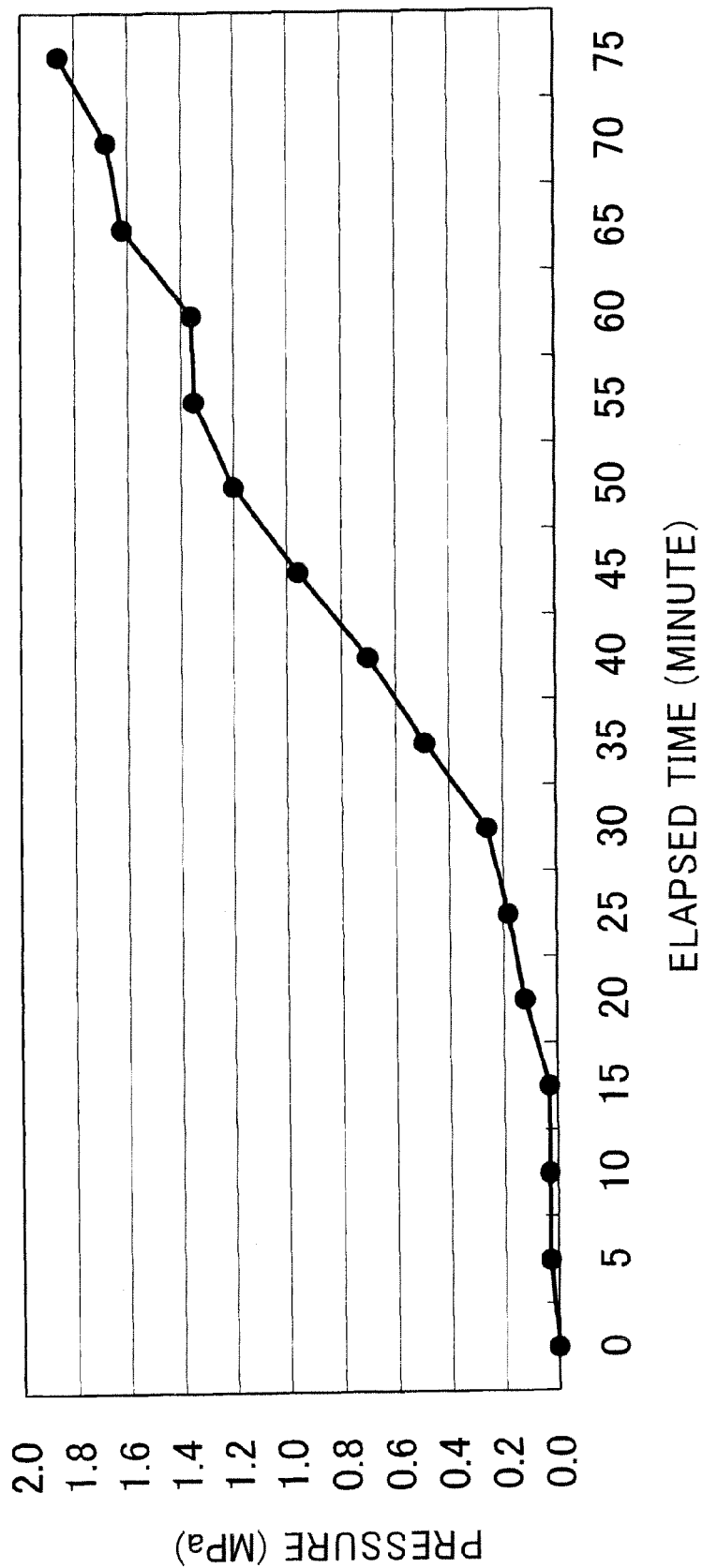
FIG. 2 is a graph showing change with time of the pressure inside the reactor due to superheated steam in Example 1.

After warming-up operation, 500 L of auxiliary water was introduced to a multi-purpose material conversion system (equipment manufactured by Rumoi Biomass Center). When the temperature at a lower portion reached 67° C., 500 kg of a dry brewer's yeast (nitrogen: 8%) was introduced. These were mixed with each other for 10 minutes, and then introduction of superheated steam was started. The dissolved oxygen was reduced by conducting a deaeration operation in such a manner that superheated steam was introduced to a head space, while the water temperature was allowed to rise and an upper exhaust valve was opened. FIGS. 1 and 2 show changes with time of the temperature and the pressure in the reactor due to the superheated steam. After treatment under conditions of a pressure of 1.6 MPa or higher and a temperature of 180° C. for 10 minutes, 1.13 t of a brewer's yeast-derived reducing mixture (liquid, nitrogen: 3%) was obtained. The oxidation-reduction potential of the mixture was −110 to −160 mV.

Example 2

Test for Investigating Effect on Plant Disease Resistance

A test was conducted for investigating an effect of the yeast-derived hydrothermal treatment product on a plant disease resistance. A liquid sample was prepared which contained 250 ppm of the yeast-derived reducing mixture obtained in Example 1, 10 μg/mL of Rifamcin, and 500 μg/ml of ampicillin. Water was used as control.

Figure 3:
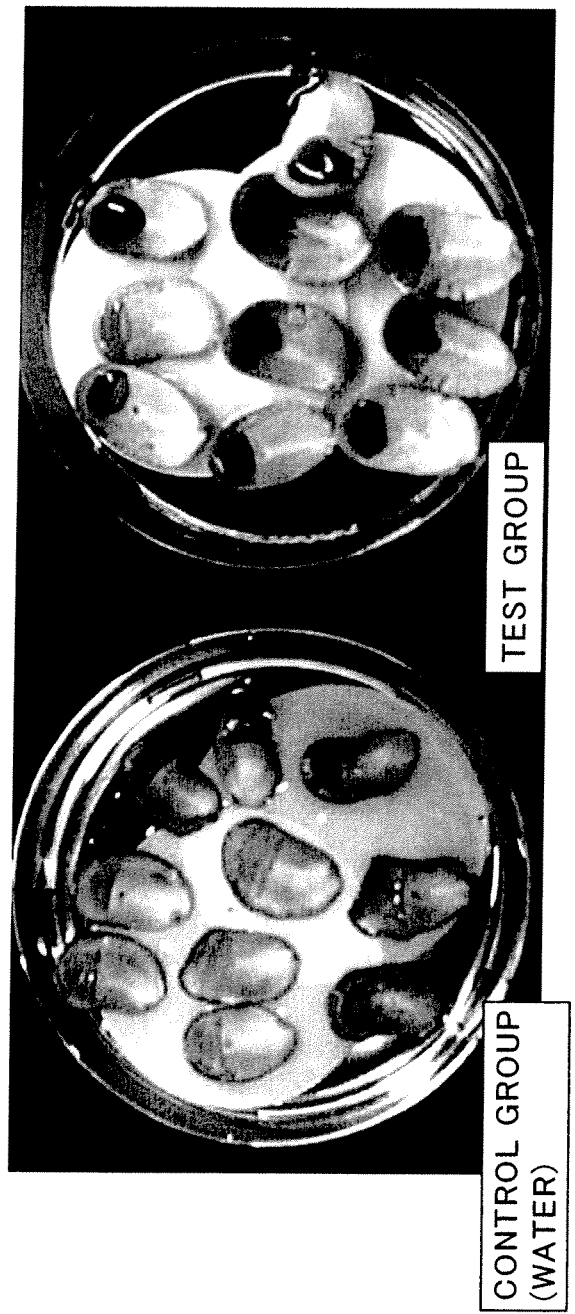
FIG. 3 is a photograph showing the results of a test for investigating an effect on plant disease resistance of Example 2.

The disease resistance was evaluated by an elicitor activity evaluation method based on the method of Yoshikawa, M., et al. (Nature 275, 546-547 (1978)). The elicitor activity is an action to induce synthesis of an antimicrobial substance such as a phytoalexin in a plant body. Specifically, soybeans (Glycine. max cv. Green Homer) were seeded in a culture soil obtained by mixing vermiculite and humus soil, and were then cultivated under fluorescent light for 10 to 14 days under conditions of a 16-hour light condition, an 8-hour dark condition, and 25° C. After that, cotyledons were cut, and the back surfaces thereof were removed with a razor, and 80 μL of the above-described liquid sample was dropped onto each cotyledon. The cotyledons were kept still for 24 hours at 25° C. under a light condition, and whether or not the wound turned red was determined. A wound which turned red indicates that the synthesis of glyceollin, which is a phytoalexin of soybean, was induced. The determination results were shown in Table 1. FIG. 3 shows a photograph used for the determination (in the photograph in FIG. 3, wounds which turned red were recognized as black portions).

As described above, it was found that the yeast-derived reducing mixture which was subjected to the hydrothermal treatment had an effect of enhancing a disease resistance of a plant.

TABLE 1

| Sample | Activity determination |
|---|---|
| Control group (water) | − |
| Test group (mixture of Example 1 was used) | + |

Example 3

Production of Fertilizer Using Brewer's Yeast-Derived Reducing Mixture

Figure 4:
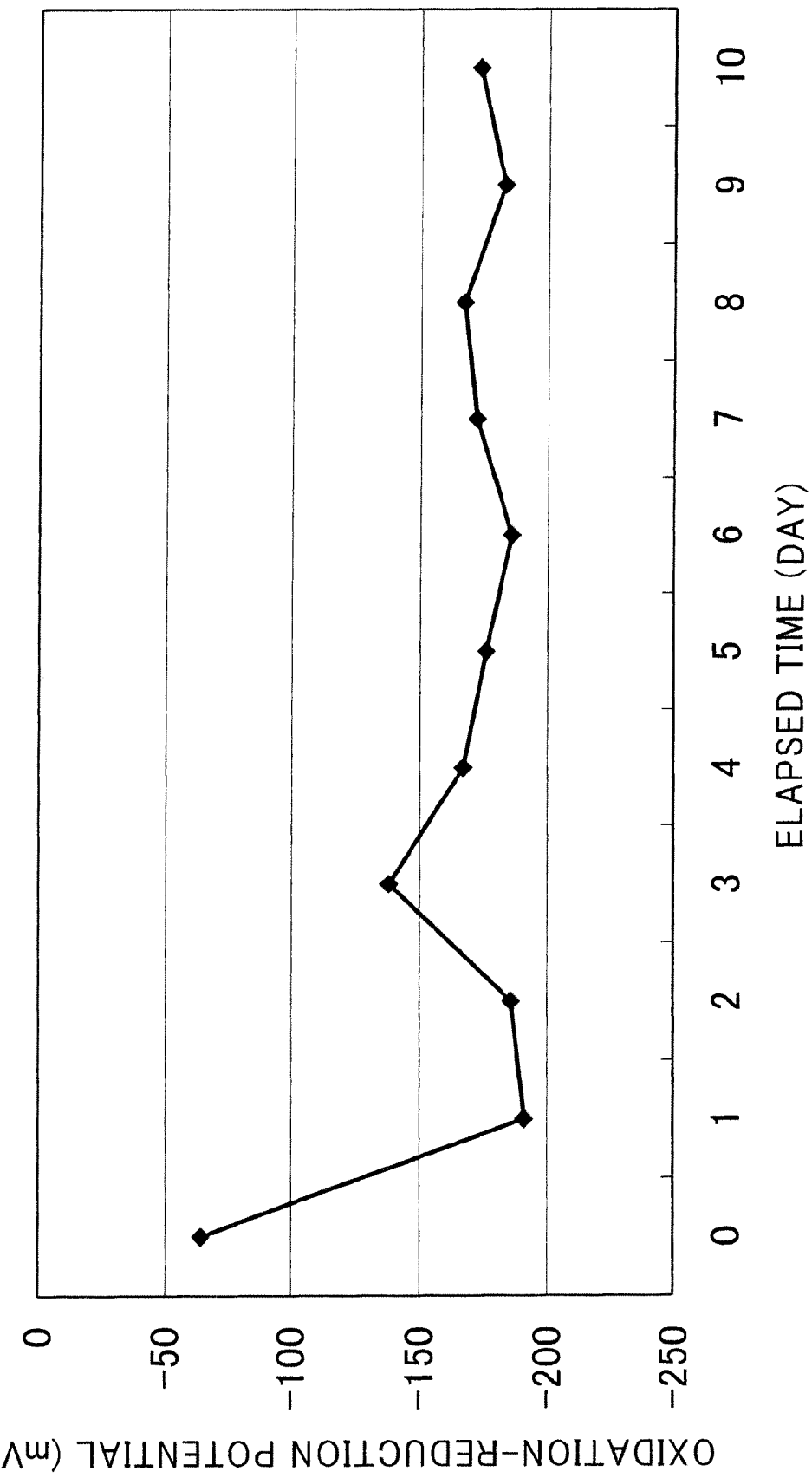
FIG. 4 is a graph showing change with time of the oxidation-reduction potential of a liquid fertilizer material in Example 3.

The brewer's yeast-derived reducing mixture of Example 1 (liquid, nitrogen: 3 w/w %), as it was, was used as a liquid active ingredient. To 500 L of a 12 w/w % urea solution, 250 L of the liquid active ingredient was added, and the materials were mixed with each other, and allowed to stand still for 10 days. Thus, a liquid fertilizer material was produced. FIG. 4 shows the change with time in the oxidation-reduction potential of the liquid fertilizer material. Note that, the oxidation-reduction potential on Day 0 is that of the 12% urea solution. As is apparent from FIG. 4, the liquid fertilizer material maintained the reducing ability even after 10 days had elapsed, and the oxidation-reduction potential was −173 mV after 10 days had elapsed.

To 1000 L of the liquid fertilizer material, 350 kg of a siliceous ore powder (trade name: North Keido, distributor: Hokkaido Natural Ltd.) was added. The materials were mixed with each other, and dried for three weeks under a condition of an air flow. Thus, a powdery fertilizer material with a water content of 35% was produced.

Example 4

Figure 5:
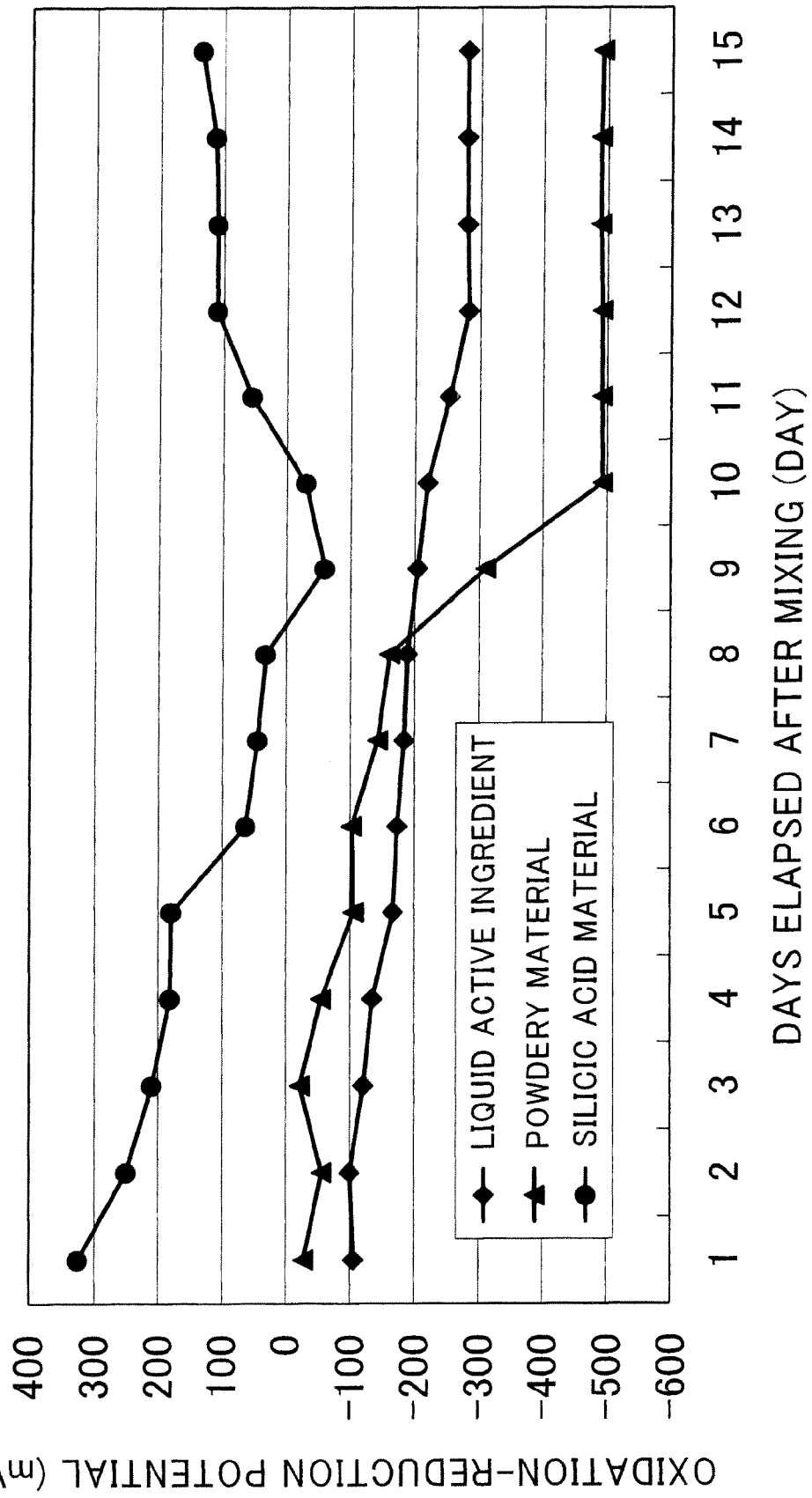
FIG. 5 is a graph showing change with time of the oxidation-reduction potential of soil in a flooded state in Example 4.

Flooding Treatment on Farm Field Soil by Use of Powdery Fertilizer Material A sandy soil with an electrical conductivity EC of 1.7 m/S was used. With 40 L of the sandy soil, 10 L of the powdery fertilizer material of Example 3 was mixed. The mixture was filled into a box-shaped well-closed container. As control groups, the siliceous ore powder was used in an amount equal to the amount of the siliceous ore powder contained in 10 L of the powdery fertilizer material, and the liquid fertilizer material was used in an amount equal to the amount of the liquid fertilizer material contained in 10 L of the powdery fertilizer material, in place of the powdery fertilizer material. Each mixture was placed in a flooding state, and was allowed to stand still for 15 days under normal temperature. The change in oxidation-reduction potential was measured for 15 days. FIG. 5 shows the results.

Comparative Example 1

Production of Brewer's Yeast-Derived Reducing Mixture in the Presence of Oxygen Into a high-pressure reactor having a capacity of 1 L, 500 g of a solution containing 5% by mass of dry brewer's yeast cell walls was introduced, and heated to 195° C. with stirring. When the temperature reached 195° C., the pressure inside the container was 1.4 MPa. Then, the reaction was allowed to proceed for 5 minutes under the conditions. The treated material immediately after being obtained had an oxidation-reduction potential of −200 mV. The chromaticity of the treated material was measured with a colorimeter in an ASCE (specular component excluded) mode. As a result, L=28.68; a=−0.45; and b=0.96.

Example 5

Production of Brewer's Yeast-Derived Reducing Mixture in the Absence of Oxygen Into a high-pressure reactor with a capacity of 1 L, 500 g of a solution containing 5% by mass of dry brewer's yeast cell walls was introduced. The air inside the reactor was replaced with nitrogen, and then the solution was heated to 195° C. with stirring. When the temperature reached 195° C., the pressure inside the reactor was 1.4 MPa. Then, the reaction was allowed to proceed for 5 minutes under the conditions. The treated material immediately after being obtained had an oxidation-reduction potential of −226 mV. Results measured with the colorimeter were as follows: L=38.65; a=4.79; and b=10.91. Comparison is made between results of Comparative Example 1 and results of Example 5 in the following Table 2. As is apparent from Table 2, the oxidation-reduction potential was lower in Example 5 than in Comparative Example 1. Moreover, on the basis of L values, the treated material of Example 5 had a lighter color than that of Comparative Example 1.

TABLE 2

| | Oxidation-reduction potential | Colorimeter | | |
| --- | --- | --- | --- | --- |
| | | L value | a value | b value |
| Comparative Example 1 | −200 mV | 28.68 | −0.45 | 0.96 |
| Example 5 | −226 mV | 38.65 | 4.79 | 10.91 |

Note that the oxidation-reduction potential is generally lowered by the Maillard reaction. In Comparative Example 1, the oxidation-reduction potential was lowered by causing the Maillard reaction (=turning to dark color). In contrast, the oxidation-reduction potential in Example 5 was lowered without causing the Maillard reaction (=remaining light color). It is easy to lower an oxidation-reduction potential by applying heat to cause the Maillard reaction. The present invention is different from conventional technologies in that the oxidation-reduction potential is lowered without causing the Maillard reaction.

Example 6

DPPH Radical Inhibition Percentage of Brewer's Yeast-Derived Reducing Mixture The brewer's yeast-derived reducing mixture obtained in Example 1 was subjected to a measurement for DPPH (1,1-diphenyl-2-picrylhydrazyl) radical quenching activity. The measurement method was as follows. The test substance was suspended in water, and the suspension was transferred to a 96-well plate where dilution series were prepared (100 μL per well). To each well, 100 μL of a 750 μM DPPH solution (dissolved in 100% methanol) was added. The plate was allowed to stand still at room temperature for 15 minutes. Thereafter, the absorbance at 550 nm was measured. The inhibition percentage was calculated from the absorbance in accordance with the following formula:

$$\text{Inhibition Percentage (\%)} = (A-B)/(C-D) \times 100$$

Figure 6:
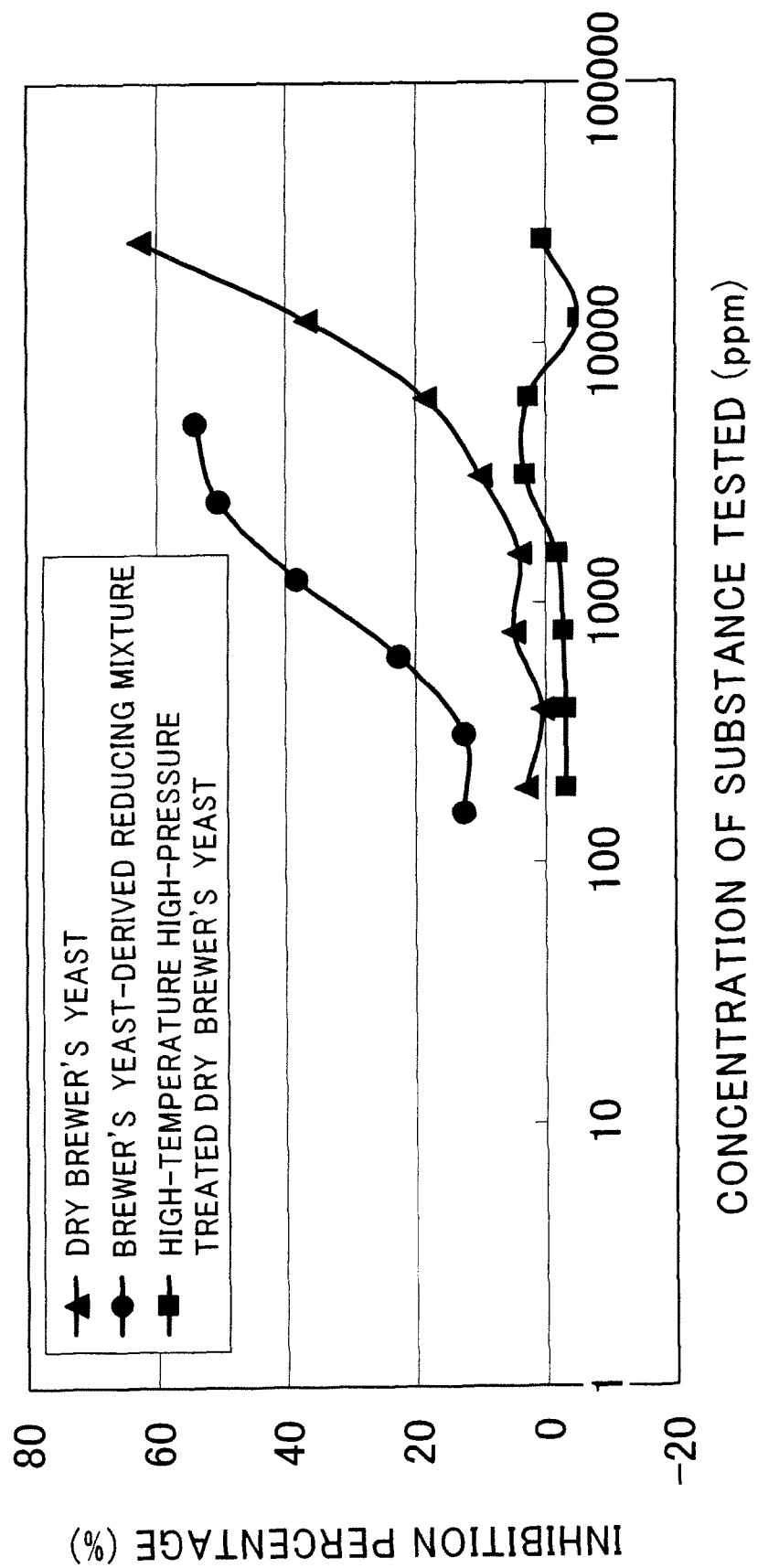
FIG. 6 is a graph showing the DPPH radical inhibition percentage of a brewer's yeast-derived reducing mixture in Example 6.

A: sample solution+enzyme, B: sample solution+no enzyme, C: water+enzyme, D: water+no enzyme FIG. 6 shows the results. Moreover, a final concentration of the test substance at which the absorbance was reduced to 50% (IC50) was determined, and this was employed as an index of the strength of the activity. For comparison, a dry brewer's yeast and a high-temperature high-pressure treated dry brewer's yeast were used. The high-temperature high-pressure treated dry brewer's yeast was obtained by treating a dry brewer's yeast under a pressurized condition of 2 atm (0.2 MPa) at 121° C. for 20 minutes. The brewer's yeast-derived reducing mixture had an IC50 of 2463 ppm, and the dry brewer's yeast had an IC50 of 18704 ppm. The high-temperature high-pressure treated dry brewer's yeast had such an extremely weak activity that it was impossible to calculate the IC50 thereof. The brewer's yeast-derived reducing mixture exhibited a remarkably stronger activity than the dry brewer's yeast and the high-temperature high-pressure treated dry brewer's yeast. These results showed that the reducing mixture derived from the material obtained by treating the brewer's yeast had a high anti-oxidation ability, and that the present invention enhanced the anti-oxidation ability of the dry brewer's yeast.

Example 7

SOD Inhibition Percentage of Brewer's Yeast-Derived Reducing Mixture

The brewer's yeast-derived reducing mixture obtained in Example 1 was subjected to a measurement for SOD (superoxide dismutase) activity. The measurement was conducted by using SOD Assay Kit-WST of Dojindo Laboratories in accordance with the standard protocol. Specifically, diluted samples were introduced into a 96-well plate (20 μL per well). Then, 200 μL of a WST (2-(4-iodophenyl)-3-(4-nitrophenyl)-5-(2,4-disulfophenyl)-2H-tetrazolium salt) solution and 20 μL of a xanthine oxidase solution were added to each of the wells. The plate was allowed to stand still at 37° C. for 20 minutes. Thereafter, the absorbance at 460 nm was measured. The inhibition percentage was calculated from the absorbance in accordance with the following formula:

Inhibition Percentage (%)=$(A-B)/(C-D) \times 100$

Figure 7:
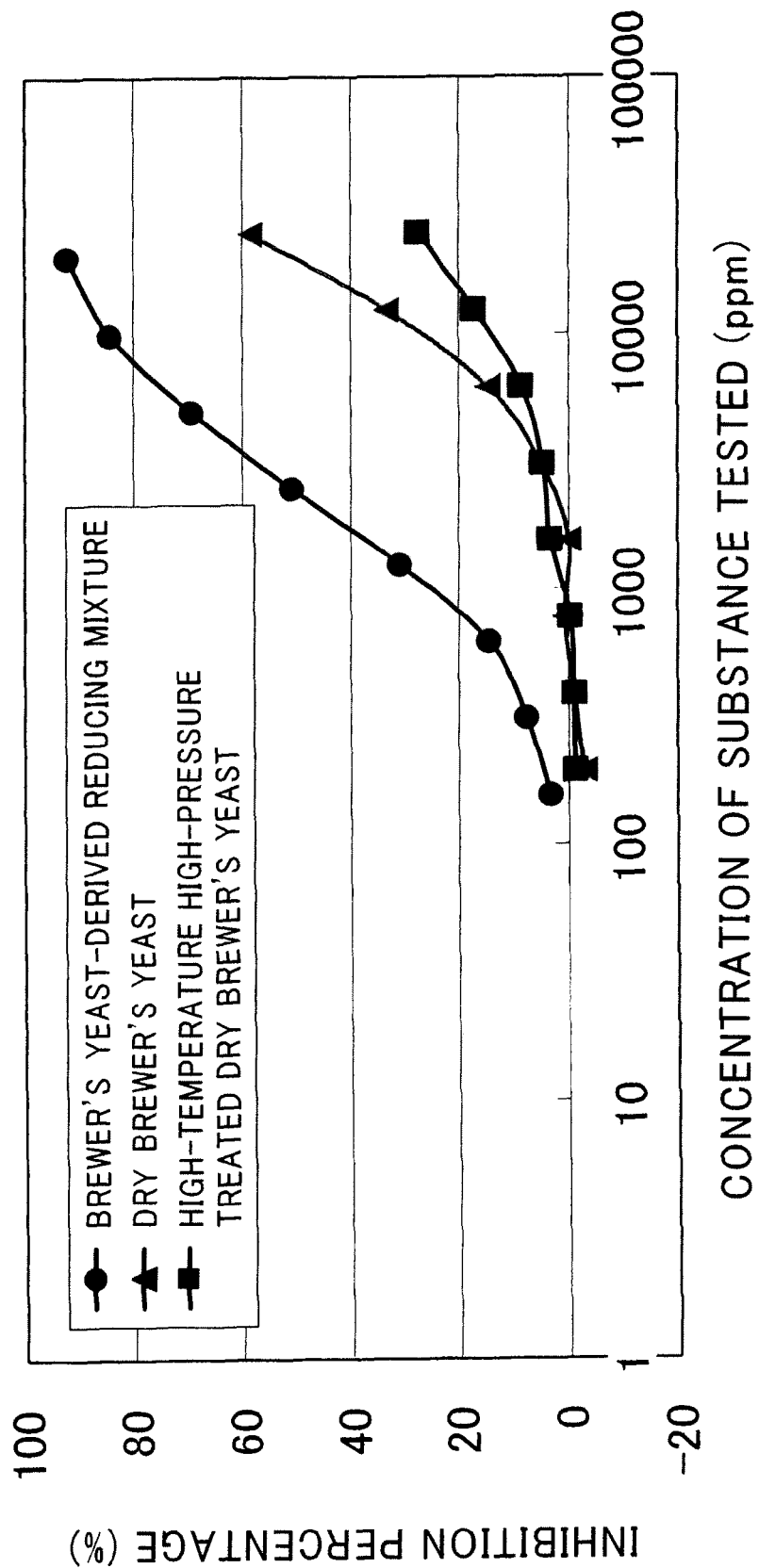
FIG. 7 is a graph showing the SOD inhibition percentage of the brewer's yeast-derived reducing mixture in Example 7.

A: sample solution+enzyme, B: sample solution+no enzyme, C: water+enzyme, D: water+no enzyme FIG. 7 shows the results. A final concentration of the test substance at which the activity was reduced to 50% (IC50) was determined, and this was employed as an index of the strength of the activity. For comparison, the same dry brewer's yeast and the same high-temperature high-pressure treated dry brewer's yeast as those in Example 6 were used. The brewer's yeast-derived reducing mixture exhibited a remarkably stronger activity than the dry brewer's yeast and the high-temperature high-pressure treated dry brewer's yeast. The brewer's yeast-derived reducing mixture had an IC50 of 2445 ppm, and the dry brewer's yeast had an IC50 of 20619 ppm. The high-temperature high-pressure treated dry brewer's yeast had such a weak activity that it was impossible to calculate the IC50 thereof. These results showed that the brewer's yeast-derived reducing mixture had a high anti-oxidation ability, and that the present invention enhanced the anti-oxidation ability of the dry brewer's yeast.

Example 8

Superheated Steam Treatment in the Presence of Siliceous Ore

A test was conducted to evaluate the effect of a catalyst during a superheated steam treatment. Powdery dry brewer's yeast cells were dissolved in water at 25 w/w %. For a test experiment, a siliceous ore (diatomite) was added at 16 w/w % as a catalyst, whereas no catalyst was added for a control experiment.

A superheated steam treatment was conducted in the same manner as in Example 1. When the temperature reached 160° C., the pressure inside the container was 1.86 MPa. Then, the reaction was allowed to proceed for 10 minutes under the conditions.

The colors of the treated materials were visually observed. The color of the treated material of the control experiment was deeper than that of the yeast liquid before the treatment. The chromaticity of the treated material of the test experiment was almost the same as that of the raw material yeast liquid before the treatment. This suggested that the siliceous ore added as the catalyst further suppressed the Maillard reaction.

Figure 8:
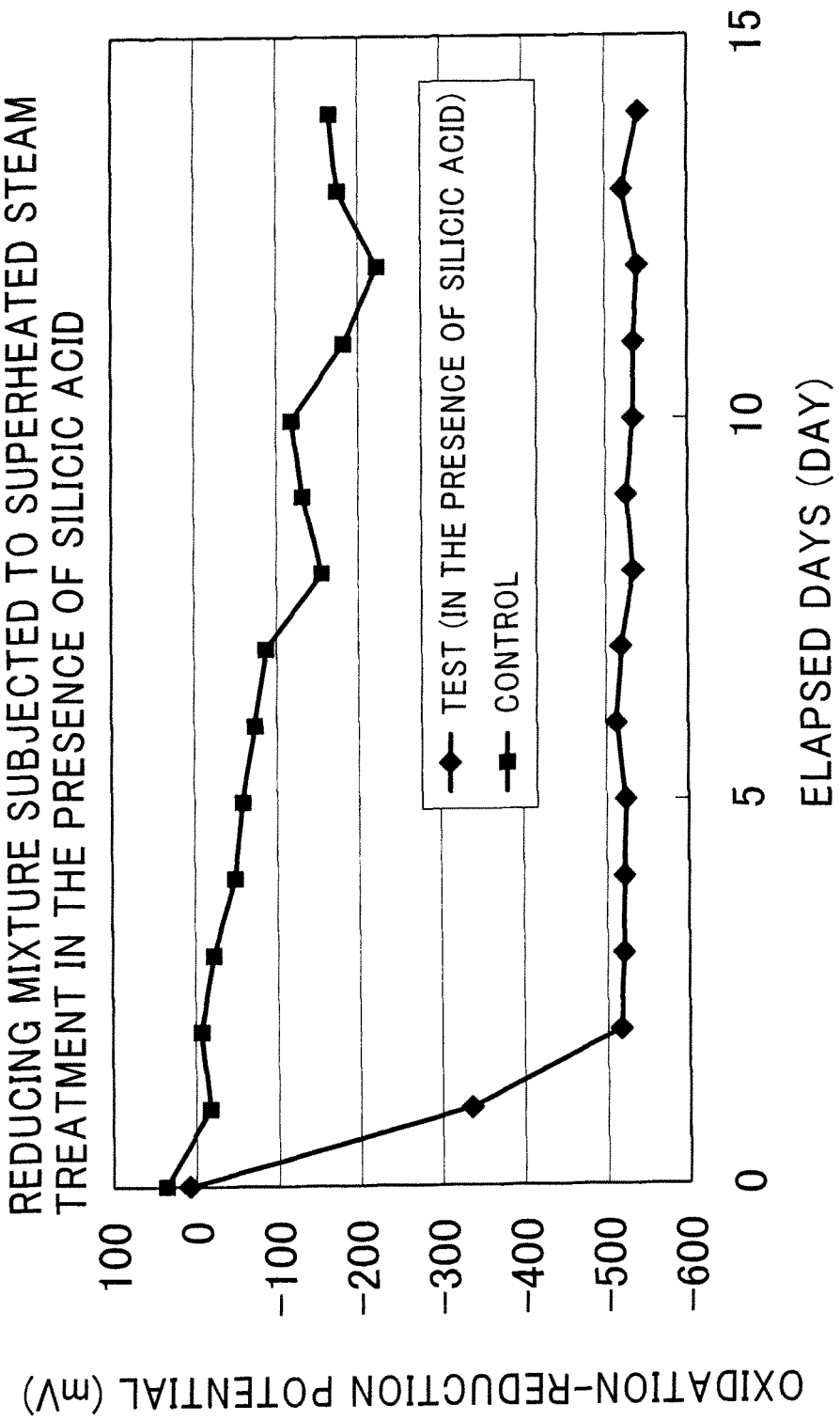
FIG. 8 is a graph showing the change with time of the oxidation-reduction potential of the brewer's yeast-derived reducing mixture in Example 8.

Next, the color of the treated materials was measured. Each of the treated materials was mixed well, and 40 ml thereof was sampled and placed into a beaker with a capacity of 100 ml. Each of the samples was photographed with a digital camera, and a printed image thereof was measured with a Lab measuring apparatus (Konica Minolta Sensing, Inc., a spectrophotometer CM-2600d) in an SCE (specular component excluded) mode. Table 3 shows the results. Each of the treated materials was diluted with water to achieve a cell concentration of 10 w/w %, and measured for change in oxidation-reduction potential (FIG. 8). The rises in oxidation-reduction potential of the reducing mixtures derived from the dry brewer's yeast 14 days after the preparation of said mixture were 3.5% of the lowest potential in the case of the test experiment, and 26.3% in the case of the control experiment.

TABLE 3

Chromaticity of Treated Material Subjected to Superheated Steam Treatment in the Presence of Siliceous Ore

| | Colorimeter | | |
|---|---|---|---|
| | L value | a value | b value |
| Test experiment | 57.88 | 2.49 | 25.09 |
| control experiment | 35.31 | 3.64 | 6.32 |

Example 9

Figure 9:
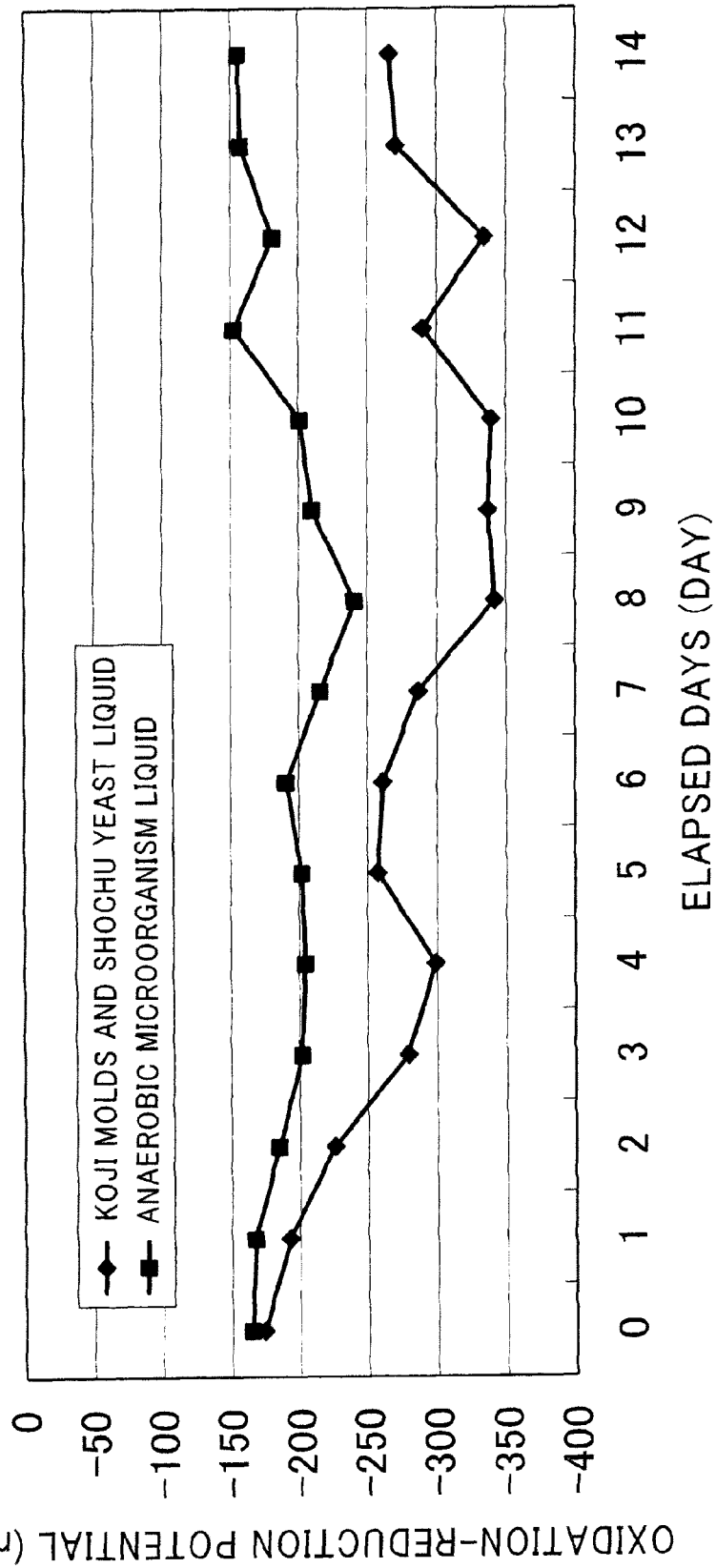
FIG. 9 is a graph showing change with time of the oxidation-reduction potential of an anaerobic microorganism and that of a Koji molds and Shochu yeast-derived reducing mixture in Example 9.

Superheated Steam Treatment on Anaerobic Microorganisms and on Koji (*Aspergillus*) Molds and Shochu (Japanese Distilled Beverage) Yeast An anaerobically digested sludge mainly containing anaerobic microorganisms (a sludge which was obtained from a human excreta treatment plant and dehydrated with a screw press to a water content of 48 to 52 w/w %), and a Shochu lees mainly containing Koji molds and Shochu yeast (having a water content of 43 to 45 w/w %) were subjected to a superheated steam treatment in the same manner as in Example 1. Note, however, that the treatment temperature was 185° C. to 190° C., and the treatment time was 20 minutes. A liquid was separated from each of the treated materials by centrifugation. The treated liquid was diluted 10-fold with water, and was measured for the oxidation-reduction potential for 14 days. FIG. 9 shows the results. The rise of the oxidation-reduction potential of the reducing mixture derived from the anaerobic microorganisms 14 days after preparation of said mixture was 35.3% of the lowest potential. Meanwhile, the rise of the oxidation-reduction potential of the reducing mixture derived from the Koji molds and Shochu yeast 14 days after preparation of said mixture was 22.2% of the lowest potential.

Comparative Example 2

Figure 10:
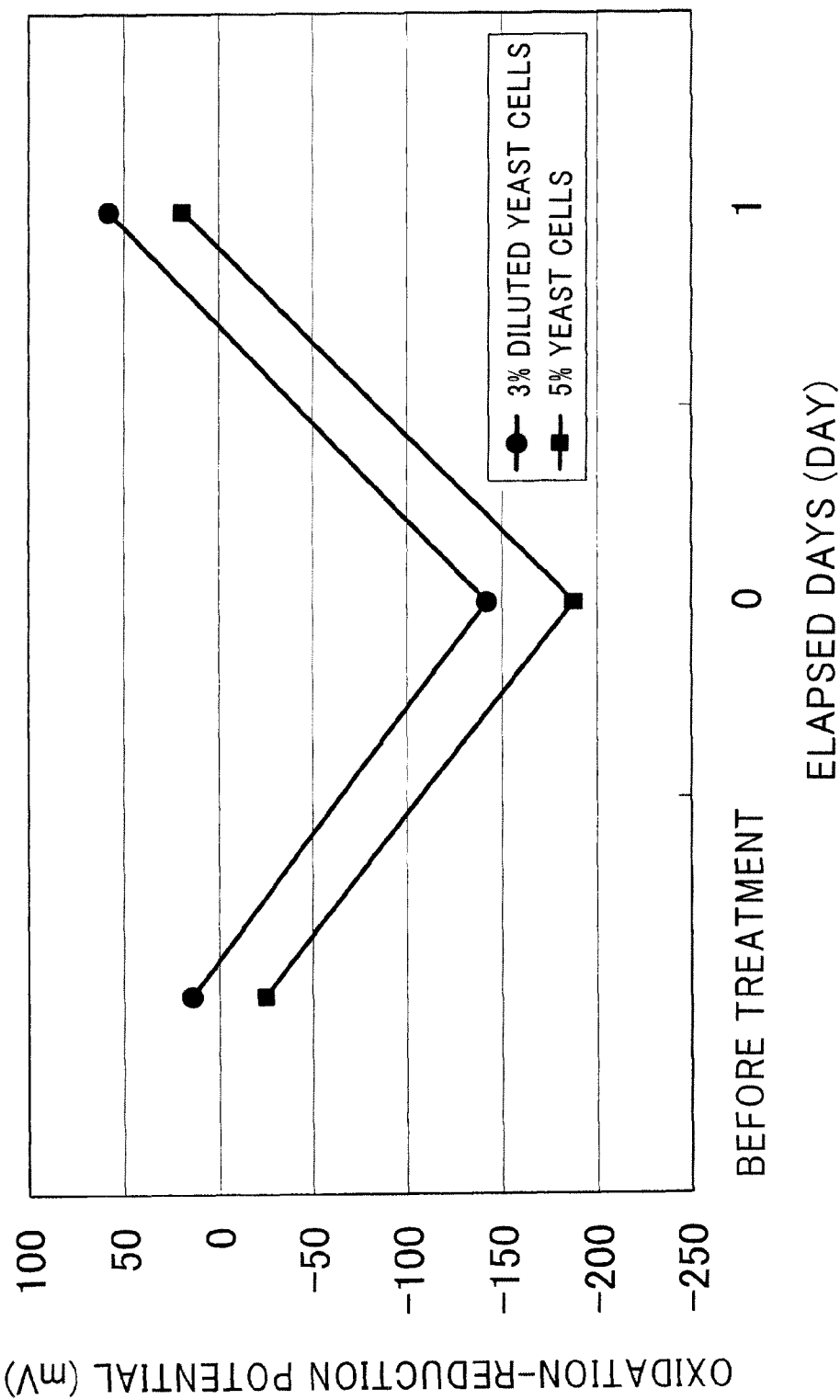
FIG. 10 is a graph showing change with time of the oxidation-reduction potential of a treated material in Comparative Example 2.

Yeast cell walls (a residue remaining after a yeast extract was produced) were diluted with purified water to 3% by mass and to 5% by mass. Into a pressure-resistant stainless steel container with a capacity of 100 ml, 50 ml of the diluted yeast cell wall liquid was filled, and heated in a thermostatic device. The heat treatment conditions were 205° C. and 30 minutes. After the treatment, the container was allowed to cool naturally for two hours in a tightly sealed state, then opened, and the oxidation-reduction potential of the treated material was measured. As is apparent from the graph shown in FIG. 10, the oxidation-reduction potentials of the treated materials were −142 mV to −188 mV immediately after the treatment, and rose to 0 mV or higher in one day. As described above, the oxidation-reduction potential of the treated material of the present invention was stable after the oxidation-reduction potential became 0 mV or less after the treatment. In contrast, the oxidation-reduction potential of each of the treated materials of Comparative Example 2 rose immediately, and reached 0 mV or higher in one day.

TABLE 4

Oxidation-Reduction Potential of Treated Materials

|  | Immediately after treatment | After one day |
|---|---|---|
| 3% diluted yeast cell walls | −142 | 58 |
| 5% yeast cell walls | −188 | 19 |

Example 10

Production of Powdery Material with which Brewer's Yeast Cell Wall-Derived Reducing Mixture was Blended To 100 L of the brewer's yeast cell wall-derived reducing mixture obtained in Example 1, 600 kg of a siliceous ore powder (trade name: North Keido, distributor: Hokkaido Natural Ltd.) was added. The materials were mixed with each other, and dried for three weeks under a condition of an air flow. Thus, a powdery material having a water content of 35% was produced.

Example 11

Flooding Treatment on Farm Field with Powdery Material

By use of a farm field (Biratori cho, Hokkaido) for actual production of tomato, 100 kg of the powdery material of Example 10 was mixed per 10 a of the farm field. The farm field was sufficiently flooded, and covered with a plastic sheet. For control, 2,000 kg of wheat wheat bran, which is generally used for flooding reduction sterilization, was mixed per 10 a of the farm field in place of the powdery material. The farm field was sufficiently flooded, and covered with a plastic sheet. The flooding treatment was conducted from May 7, 2009 to Jun. 6, 2009. Planting was conducted on June 18. Soil located at a depth of 20 cm was sampled on each of May 14, May 25, and June 6, and the oxidation-reduction potential of a solution obtained by diluting the sampled soil 10-fold with tap water was measured. Moreover, soil located at a depth of 20 cm was sampled on each of May 25, June 18, July 18, and August 18, and was measured for the amount (cells/g dry soil) of *Fusarium* bacteria, which are soil pathogenic bacteria. Tables 5 and 6 show the results. Here, the untreated area was an area where only the flooding treatment was conducted without introducing the material. The oxidation-reduction potential of the test area was lower than that of the untreated area. Moreover, the sterilization effect on the *Fusarium* bacteria after the flooding reduction sterilization of the test area was high, and was at the same level as that of the wheat bran area. Proliferation of the *Fusarium* bacteria after the planting was more suppressed in the test area than in the untreated area and the wheat bran area.

TABLE 5

Change in Oxidation-Reduction Potential (mV)

|  | May 14 | May 25 | June 6 |
|---|---|---|---|
| Untreated area | 269 | 244 | 270 |
| Wheat bran area | −98 | −160 | 86 |
| Test area | −92 | −149 | 51 |

TABLE 6

Change in Amount of *Fusarium* Bacteria (cells/g dry soil)

|  | Before treatment | May 25 | June 18 | July 18 | August 18 |
|---|---|---|---|---|---|
| Untreated area | $2.7 \times 10^5$ | $2.4 \times 10^3$ | $9.7 \times 10^2$ | $2.8 \times 10^2$ | $3.7 \times 10^2$ |
| Wheat bran area | $2.7 \times 10^5$ | $1.4 \times 10^2$ | 3 | $4.9 \times 10^2$ | $9.8 \times 10^2$ |
| Test area | $2.7 \times 10^5$ | $1.4 \times 10^2$ | 1 | $3.6 \times 10$ | $5.1 \times 10$ |

Example 12

Flooding Treatment on Farm Field with Powdery Material

Nematodes isolated from a farm field (Chiba Prefecture) for actually producing tomato were cultured in an agar medium, and then the gel was cut out and transferred to a Petri dish. The gel was immersed in a 5% aqueous solution of the powdery material of Example 10 to achieve a flooding state. For an untreated group for control, the gel was immersed in distilled water to achieve a flooding state. Ten days later, 25 nematodes in each of the test group and the untreated group were observed with a microscope, and evaluated for motility and classified into the following five grades: 0 (the nematodes did not move at all) to 4 (the nematodes moved vigorously).

0: The nematodes did not move at all.

1: Only end portions of the nematodes moved slightly.

2: The whole bodies of the nematodes moved slightly.

3: The whole bodies of the nematodes moved without location change.

4: The nematodes moved vigorously with location change.

Figure 11:
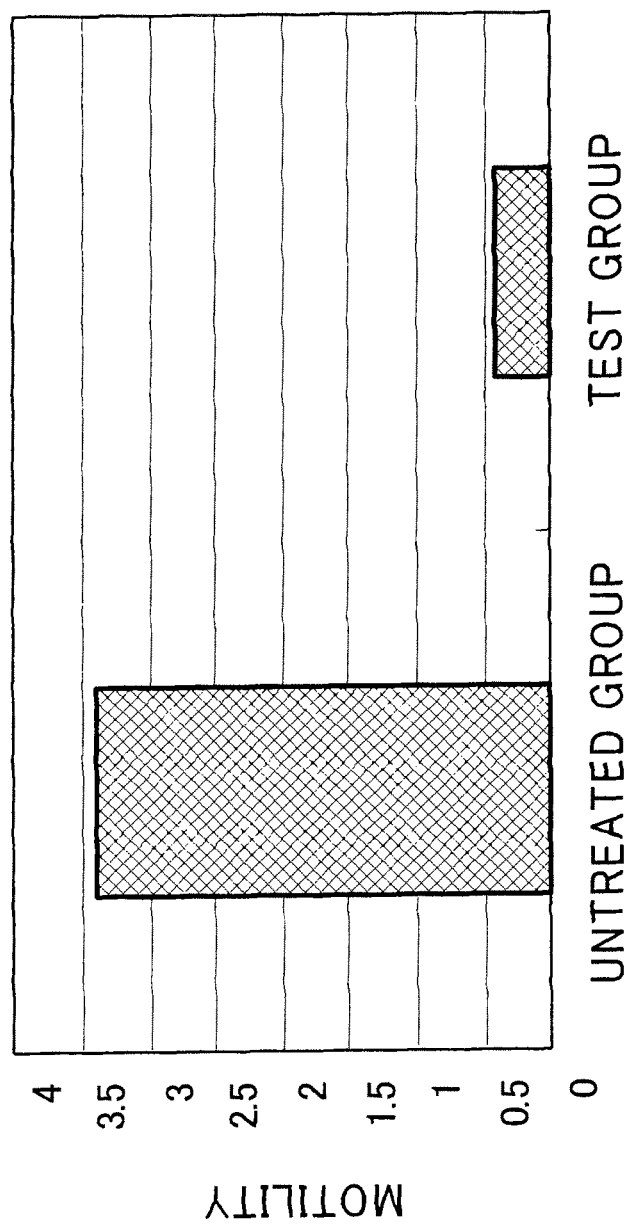
FIG. 11 is a graph showing comparison of the motilities of nematodes in Example 12.

FIG. 11 shows the results. In contrast to the untreated group, the activity of the nematodes in the test group was greatly suppressed.

Example 13

Growth Promotion Effect on *Molokheiya*

Figure 12:
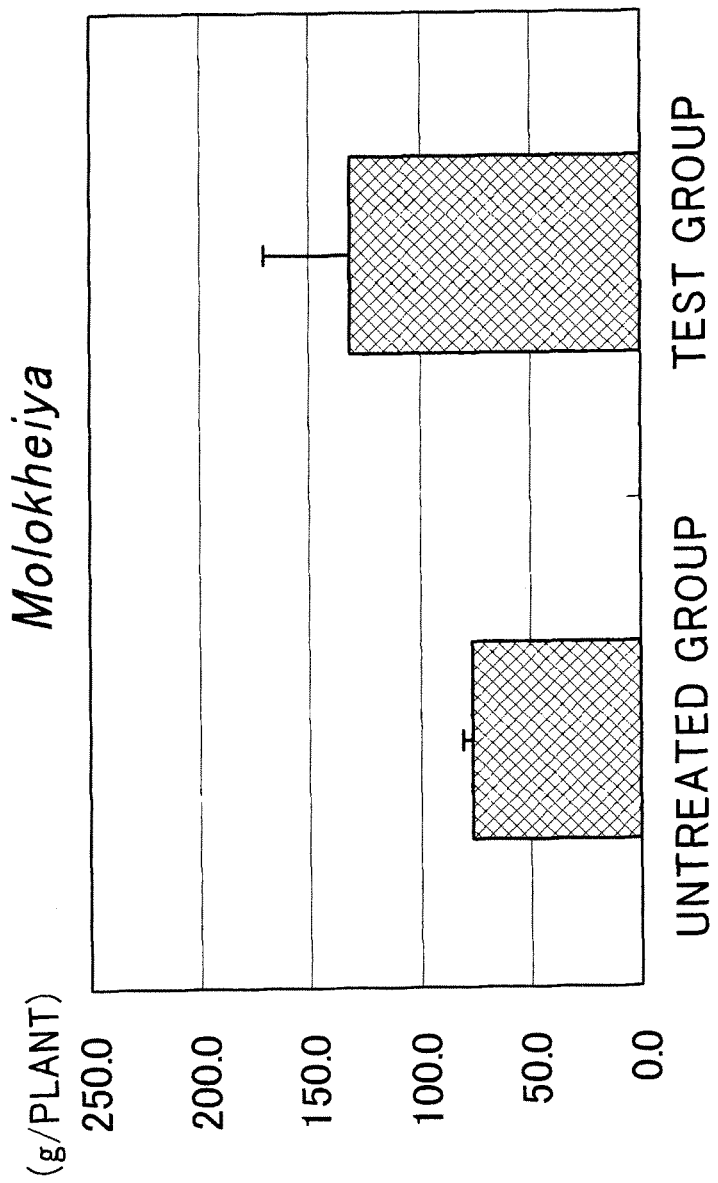
FIG. 12 is a graph showing comparison of the weights of the edible part of *Molokheiya* in Example 13.

By use of a farm field (Moriya City, Ibaraki Prefecture) for actual production of *Molokheiya,* 1000 kg of the powdery material of Example 11 was mixed per 10 a of the farm field. *Molokheiya* was planted on Jun. 17, 2009, and harvested on Aug. 3, 2009. The weight of the edible part was measured. FIG. 12 shows the results. The yield in the test area was higher by approximately 74% than in the untreated area.

Example 14

Growth Promotion Effect on Garland *Chrysanthemum*

By use of a farm field (Moriya City, Ibaraki Prefecture) for actual production of garland *chrysanthemum,* 1000 kg of the powdery material of Example 11 was mixed per 10 a of the farm field. Garland *chrysanthemum* was planted on Jun. 17, 2009, and harvested on Aug. 3, 2009. The weight of the edible part was measured. FIG. 13 shows the results. The yield in the test area was higher by approximately 70% than in the untreated area.

Example 15

Bacteriostatic Action on *Staphylococcus aureus*

The powdery material of Example 11 was added to a culture medium (0.08% of Nutrient Broth and 0.05% of Yeast Extract) at 20% (w/v). Two days later, *Staphylococcus aureus* ($4.1 \times 10^9$ cells/ml) was inoculated, and subjected to static culture at 25° C. for two days. Then, the number of viable cells was determined. Table 7 shows the results. The amount of the *Staphylococcus aureus* bacteria of the untreated experiment was increased. In contrast, the proliferation of the *Staphylococcus aureus* bacteria was suppressed in the test experiment, and the amount of the bacteria was reduced.

TABLE 7

Change in amount of *Staphylococcus aureus* bacteria (cells/ml)

|  | At inoculation | After culturing |
|---|---|---|
| Untreated experiment (culture medium) | $4.1 \times 10^9$ | $6.4 \times 10^{10}$ |
| Test experiment | $4.1 \times 10^9$ | $7.4 \times 10^6$ |

Example 16

Bacteriostatic Actions on *Staphylococcus chromogenes* and *Bacillus thuringiensis*

The powdery material of Example 11 was added to a culture medium (0.08% of Nutrient Broth and 0.05% of Yeast Extract) at 20% (w/v). Ten days later, *Staphylococcus chromogenes* ($5.6 \times 10$ cells/ml) and *Bacillus thuringiensis* ($1.8 \times 10$ cells/ml) which were isolate from milk of a breast inflammation cow were inoculated, and subjected to static culture at 25° C. for two days. Then, the total number of viable cells was determined.

Table 8 shows the results. The amount of bacteria in the untreated experiment was greatly increased, whereas the bacteria did not proliferate at all in the test experiment.

TABLE 8

Change in Amount of Bacteria of *Staphylococcus chromogenes* and *Bacillus thuringiensis* (cells/m )

|  | At inoculation | After culturing |
|---|---|---|
| Untreated experiment (culture medium) | $7.2 \times 10$ | $3.5 \times 10^6$ |
| Test experiment | $7.2 \times 10$ | 0 |

Example 17

Yield Increase Effect on Cherry Tomato

A farm field (Moriya City, Ibaraki Prefecture) for actual production of cherry tomato was used. Cherry tomato was seeded on Mar. 4, 2009, and planted on April 6. After the planting, the liquid material of Example 11 diluted 1000-fold was administered thorough a water feeding tube once a week. The cherry tomato was harvested from May 25 to August 5, and the total yields were compared with each other. FIG. 14 shows the results. The yield in the test area was higher by approximately 12% than that of the untreated area.

The invention claimed is:

1. A method for producing a microorganism-derived reducing mixture having an oxidation-reduction potential of 0 mV or less, the method comprising subjecting a microorganism in water or a microorganism component in water to superheated steam treatment in the absence of oxygen for a time sufficient to obtain a liquid microorganism-derived reducing mixture, wherein said superheated steam treatment is conducted with superheated steam having both a pressure of 0.9 MPa to 1.9 MPa and a temperature of 150° C. to 210° C.

2. The production method according to claim 1, wherein the microorganism is a yeast.

3. The production method according to claim 1, wherein the microorganism component is a yeast extract.

4. The production method according to claim 1, wherein the microorganism or the microorganism component is one or a combination of a plurality of members selected from the group consisting of brewer's yeast slurrys, pressed brewer's yeasts, dry brewer's yeasts, brewer's yeast suspensions, dry yeast cell walls, yeast cell wall suspensions, and brewer's yeast-containing inorganic materials.

* * * * *